United States Patent [19]

Jaeger

[11] Patent Number: 4,904,780

[45] Date of Patent: Feb. 27, 1990

[54] PROCESS FOR THE MONOACYLATION OF WATER-SOLUBLE ORGANIC AMINO COMPOUNDS

[75] Inventor: Horst Jaeger, Leverkusen, Fed. Rep. of Germany

[73] Assignee: Bayer Aktiengesellschaft, Leverkusen, Fed. Rep. of Germany

[21] Appl. No.: 224,971

[22] Filed: Jul. 27, 1988

[30] Foreign Application Priority Data

Aug. 15, 1987 [DE] Fed. Rep. of Germany ....... 3727253

[51] Int. Cl.$^4$ .......................................... C07D 251/44
[52] U.S. Cl. .................................................. 544/211
[58] Field of Search ........................................ 544/211

[56] References Cited

U.S. PATENT DOCUMENTS

| | | | |
|---|---|---|---|
| 4,189,570 | 2/1980 | Bonometti et al. | 544/211 |
| 4,189,576 | 2/1980 | Altorfer et al. | 544/211 |
| 4,225,709 | 9/1980 | Hegar et al. | 544/211 |
| 4,361,698 | 11/1982 | Otten et al. | 544/211 |
| 4,740,597 | 4/1988 | Franke et al. | 544/211 |

FOREIGN PATENT DOCUMENTS 0094538 11/1983 European Pat. Off. .
2903594 8/1980 Fed. Rep. of Germany .

*Primary Examiner*—John M. Ford
*Attorney, Agent, or Firm*—Sprung Horn Kramer & Woods

[57] ABSTRACT

An improved process for the monoacylation of water-soluble organic amines using 2,4,6-trifluorotriazine in aqueous medium consists in carrying out the reaction in the presence of inorganic and/or organic water-soluble salts and/or water-miscible organic solvents at temperatures below 0° C.

6 Claims, No Drawings

PROCESS FOR THE MONOACYLATION OF WATER-SOLUBLE ORGANIC AMINO COMPOUNDS

The monoacylation of water-soluble organic amino compounds using 2,4,6-trifluorotriazine (cyanuric fluoride) is in general carried out in such a way that cyanuric fluoride is metered into an amino compound in aqueous medium and a temperature of 0° to 5° is maintained by addition of ice or external cooling (compare DE-OS (German Published Specification) 2,746,109, EP-A 0,172,790, DE-OS (German Published Specification) 2,747,011, DE-OS (German Published Specification) 2,903,594). This condensation frequently proceeds non-uniformly since, owing to the high reactivity of the primarily resulting monocondensation products of cyanuric fluoride, these immediately react further with non-acylated amino compound still present to give dicondensation products.

The present invention now relates to the monoacylation of water-soluble organic amines using 2,4,6-trifluorotriazine in aqueous medium at temperatures below 0° C. in the presence of inorganic and/or organic water-soluble salts and/or water-miscible organic solvents.

The process is preferably carried out in such a way that the amine is introduced into aqueous medium and the triazine is metered in below 0° C.

The process can also be carried out as a continuous process, for example by leading amine and triazine simultaneously and continuously into the reaction space in the amount required for the desired throughput and continuously removing the reaction products formed from the reaction space (compare DE-OS (German Published Specification) 2,746,109) or by leading amine and triazine simultaneously and continuously into a first reactor, performing an intensive mixing there and subsequently leading the reaction mixture into a second reactor in which only small back-mixing but good radial mixing occurs and carrying the reaction to completion there (compare EP 172,790).

Particularly suitable aqueous media here are mixtures of water and inorganic or organic salts or water-soluble organic solvents.

The hydrofluoric acid released in the reaction can be neutralized in a customary manner using alkaline-reacting compounds.

Triazine and amine are in general brought to reaction in a molar ratio of 0.8:1 to 1.5:1, preferably 1:1 to 1.2:1, in particular 1.1:1 to 1.08:1.

The amines are preferably present in solution and are preferably employed in the form of their neutral alkali metal salts. The process according to the invention is preferably suitable for the acylation of chromophoric water-soluble organic amines, in particular the amino group-containing azo, anthraquinone, phthalocyanine, formazan or dioxazine dyes known from the chemistry of reactive dyes.

The process is in particular also suitable for the acylation of non-chromophoric water-soluble organic amines, in particular of water-soluble arylamines, for example those sulpho group-containing arylamines of the benzene or naphthalene series which can have substituents such as alkyl, alkoxy, halogen, amino, hydroxyl and carboxyl, which are intermediates for the production of fibre-reactive dyes.

The 2-amino-4,6-difluorotriazines obtainable according to the process according to the invention are in general reacted with a further mole of amine to give the final dye or the intermediate used for the final dye.

Particularly suitable starting amines for the process according to the invention are, for example, the following: 1-amino-8-hydroxy-naphthalene-3,6-disulphonic acid, 1-amino-8-hydroxy-naphthalene-4,6-disulphonic acid, 2-amino-5-hydroxy-naphthalene-7-sulphonic acid, 2-amino-8-hydroxy-naphthalene-6-sulphonic acid, 2-methylamino-5-hydroxy-naphthalene-7-sulphonic acid, 1-amino-8-hydroxy-naphthalene-4-sulphonic acid, 1-aminobenzene-3-sulphonic acid, 1-aminobenzene-4-sulphonic acid, 1-amino-4-methylbenzene-3-sulphonic acid, 1-amino-4-methoxybenzene-3-sulphonic acid, 4-aminobenzoic acid, 1-aminonaphthalene-6-sulphonic acid, 2-aminonaphthalene-5-sulphonic acid, 2-aminonaphthalene-6-sulphonic acid, 2-aminonaphthalene-8-sulphonic acid, 1,3-diaminobenzene-4-sulphonic acid, 1,4-diaminobenzene-2-sulphonic acid and 2-aminoethanesulphonic acid.

The process according to the invention is particularly suitable for the reaction of cyanuric fluoride with 2-amino-5-hydroxynaphthalene-7-sulphonic acid, 2-amino-8-hydroxynaphthalene-6-sulphonic acid, 1-amino-8-hydroxynaphthalene-4,6-disulphonic acid or, above all, 1-amino-8-hydroxynaphthalene-3,6-disulphonic acid, where these are preferably employed in the form of their neutral alkali metal salts (Li, Na, K).

Preferably, the acylations are carried out in water-salt mixtures which, owing to lowering of freezing points are particularly suitable for carrying out the reaction.

Suitable salts are, in particular, inorganic salts such as halides, sulphates and phosphates of alkali metals and alkaline earth metals, such as lithium chloride, sodium chloride, potassium chloride, magnesium chloride, calcium chloride, sodium sulphate, potassium sulphate, magnesium sulphate, disodium hydrogen phosphate, sodium dihydrogen phosphate, potassium dihydrogen phosphate, dipotassium hydrogen phosphate, sodium fluoride, potassium fluoride and also ammonium chloride or ammonium sulphate.

Suitable organic salts are, for example, quaternary ammonium salts such as tetra-alkylammonium halides, for example tetramethylammonium chloride, tetraethylammonium chloride or salts or organic sulphonic acids, in particular those of alkyl-, and arylsulphonates, in particular $C_1$–$C_4$-alkylsulphonates and those of the benzene and naphthalene series, where Li, Na and K are preferably suitable as cations. The salts of methane-, benzene- or naphthalenesulphonic acids are particularly suitable (mono-, di- or trisulphonic acids).

The choice and amount of the salt depends in this case on the solubility of the water-soluble organic amine to be acylated. Mixtures of salts can also be used. The amount can vary within a wide range. In general, it is between 1 and 30% by weight relative to the weight of the reaction solution or suspension, preferably between 2 and 15% by weight, in particular between 3 and 10% by weight.

Examples of organic water-soluble compounds which may be mentioned are the following: alcohols, such as ethanol, isopropanol, ethylene glycol, diethylene glycol, ethers such as glycol dimethyl ether, diethylene glycol dimethyl ether, glycol monomethyl ether, butyl glycol, acid amides, such as formamide, dimethylformamide, urea, tetramethylurea, caprolactam, N,N'-dimethylurea and sulpholane. The amount can also vary within a wide range here. In general, it is between 1% and 50% by weight, relative to the total weight of the reaction solution or suspension, preferably between 5 and 30% by weight, in particular between 10 and 20% by weight.

During the condensation, the temperature is below 0°, preferably between −1° and −20°, in particular between −2° and −15°, in particular between −4° and −12°.

This temperature can be achieved, for example, by cooling externally with a cooling brine. However, a procedure can also be used in which the water-soluble organic amino compound to be acylated is introduced in water without additional cooling, salt is added and ice is thrown in, as a result of which cooling to below 0° occurs. This effect is in general sufficient to keep the temperature during the acylation below 0°.

For the neutralization of the hydrofluoric acid released, oxides, hydroxides, hydrogen carbonates, carbonates or phosphates of alkali metals and alkaline earth metals; for example lithium hydroxide, lithium carbonate, sodium hydroxide, sodium carbonate, sodium hydrogen carbonate, potassium hydroxide, potassium carbonate, magnesium hydroxide, magnesium carbonate, calcium oxide, calcium hydroxide and calcium carbonate are used in particular as the alkaline-reacting substance. In principle, a tertiary aliphatic amine, such as triethylamine or triethanolamine is also suitable.

The indicated formulae are those of the free acids, to which the weight data also relate. The aromatic sulphonic acids are in general present as salts, in particular the sodium, potassium or lithium salts.

The temperature data are in °C.

EXAMPLE 1

46.2 g of H acid = 1-amino-8-hydroxy-naphthalene-3,6-disulphonic acid (monosodium salt) are dissolved in 120 ml of water with 30 ml of 11% strength lithium hydroxide solution, as a result of which a pH of 6.0 to 6.5 is set. This solution (190 ml) is poured into a Dewar vessel and 19 g of lithium chloride are added as a result of which the temperature climbs to 38°. 10 g of boric acid are subsequently added. The temperature is lowered to −8° by throwing in 300 g of ice. 19.6 g of trifluorotriazine are now added dropwise in the course of 20 minutes, first allowing the pH to fall from 6.0 to 6.5 down to 4.3 and, after reaching this value, keeping the pH between 4.0 and 4.5 by adding lithium hydroxide solution dropwise. During the acylation a precipitate appears, which goes into solution again towards the end of the acylation. The mixture is now tested for complete acylation of the H acid and, if necessary, 1–2 g of trifluorotriazine are added. After completion of the acylation, the reaction temperature is −5°. 13.5 g of aniline are subsequently added dropwise, as a result of which the temperature climbs above 0°. The pH is adjusted to 5.5 by addition of lithium hydroxide solution and the condensation with aniline is carried to completion at a temperature of 0° to 10°. The condensation product is partly precipitated. It corresponds to the following formula

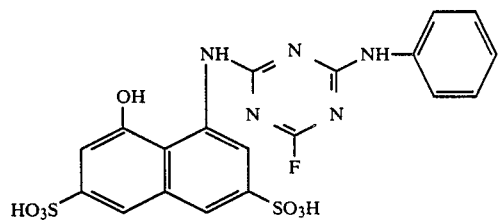

It is present as the mixed lithium/sodium salt.

A diazonium salt suspension at 0° to 5°, which was obtained in a customary manner by diazotization of 0.145 mol of 2-aminonaphthalene-1,5-disulphonic acid, is added to the suspension obtained. It is coupled to completion in the pH range from 6 to 7.5 at a maximum of 10°.

The dye of the formula

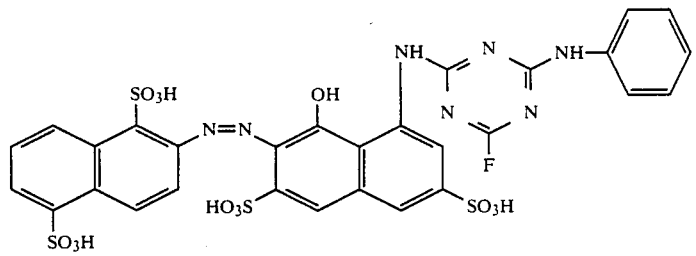

is obtained in the form of the mixed Li/Na salt in good yield. It colours cotton a clear red shade which is fast to washing.

In an otherwise equivalent procedure, the dye described previously, which is in addition still contaminated with red by-products, is obtained in clearly lower yield by the hitherto customary process, i.e. by carrying out the condensation of cyanuric fluoride with 1-amino-8-hydroxynaphthalene-3,6-disulphonic acid at 0°–5° C.

EXAMPLE 2

46.2 g of H acid = 1-amino-8-hydroxy-naphthalene-3,6-disulphonic acid (monosodium salt) are dissolved in 150 ml of water with 30 ml of 11% strength lithium hydroxide solution, as a result of which a pH of 6.0 to 6.5 is set. 22 g of lithium chloride are added to this solution, as a result of which it is warmed to 35°–40° C. The pH is then lowered to 4.8 by adding dil. hydrochloric acid dropwise and the mixture is subsequently cooled externally to −10° C. using a cooling brine. 19.6 g of trifluorotriazine are now added dropwise at −8° to −11° C. in the course of 20 minutes, as a result of which the pH is first allowed to fall from 4.8 to 4.0 and after reaching this value it is kept between 4.0 and 4.5 by dropwise addition of lithium hydroxide solution. During the acylation a precipitate appears, which goes into solution again towards the end of the acylation. The mixture is now tested for complete acylation of the H acid and, if necessary, 1–2 g of trifluorotriazine are added. After completion of the acylation, the reaction temperature is −10°. 13.5 g of aniline are subsequently added dropwise, as a result of which the temperature climbs above 0°. The pH is adjusted to 5.5 by addition of lithium hydroxide solution and the condensation is carried to completion at a temperature of 0° to 5° with aniline. The condensation product is partly precipitated. It corresponds to the following formula

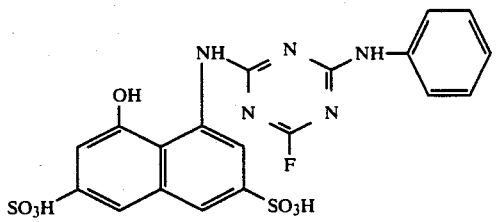

It is present as the mixed lithium/sodium salt.

The dye described in Example 1 is likewise obtained in good yield by diazotizing 2-amino-naphthalene-1,5-disulphonic acid and coupling.

I claim:

1. In a process for the monoacylation of an aromatic amino-sulphonic acid by reaction of said aminosulphonic acid with 2,4,6-trifluorotriazine in aqueous medium, the improvement wherein the monoacylation reaction is carried out at temperatures below 0° C. in the presence of inorganic and/or organic water-soluble salts and/or water-miscible organic solvents.

2. Process according to claim 1, wherein the reaction is carried out at −1° to −20° C.

3. Process according to claim 1, wherein the reaction is carried out at −2° to −15° C.

4. Process according to claim 1, wherein the reaction is carried out at −4° to −12° 1 C.

5. Process according to claim 1, wherein a mixture of water and inorganic salt is used as the aqueous medium.

6. Process according to claim 1, wherein the aminosulphonic acid is selected from the group consisting of 1-amino-8-hydroxy-naphthalene-3,6- or -4,6-disulphonic acid, 2-amino-5-hydroxynaphthalene-7-sulphonic acid and 2-amino-8-hydroxynaphthalene-6-sulphonic acid.

* * * * *

UNITED STATES PATENT AND TRADEMARK OFFICE
CERTIFICATE OF CORRECTION

PATENT NO. : 4,904,780

DATED : February 27, 1990

INVENTOR(S) : Horst Jaeger

It is certified that error appears in the above-identified patent and that said Letters Patent is hereby corrected as shown below:

Col. 6, line 13            After "12°" delete "1"

Signed and Sealed this

Third Day of March, 1992

*Attest:*

HARRY F. MANBECK, JR.

*Attesting Officer*      *Commissioner of Patents and Trademarks*